United States Patent [19]
Veith et al.

[11] Patent Number: 5,926,882
[45] Date of Patent: *Jul. 27, 1999

[54] FABRICATING ASSEMBLY AND CASTING APPARATUS FOR PROSTHETIC AND ORTHOTIC DEVICES

[75] Inventors: Ulrick A. Veith, West Simsbury; Willi W. Veith, Farmington, both of Conn.

[73] Assignee: V-Tech Systems Corp., West Hartford, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/609,857

[22] Filed: Mar. 1, 1996

[51] Int. Cl.$^6$ .................................................. B23Q 1/25
[52] U.S. Cl. .................................. 5/658; 269/76; 269/71; 269/45
[58] Field of Search ................................. 5/658, 81.1 R; 297/411.35, 411.36, 411.2, 338; 298/121, 132, 218.4; 267/45, 71, 76; 128/845, 846

[56] References Cited

U.S. PATENT DOCUMENTS

| | | | |
|---|---|---|---|
| 2,879,059 | 3/1959 | Sandefur | 269/71 |
| 4,145,006 | 3/1979 | Webb | 269/71 |
| 4,392,645 | 7/1983 | Westphal | 269/45 X |
| 4,624,245 | 11/1986 | Mullin et al. | 5/658 X |
| 4,647,001 | 3/1987 | Sarette et al. | 269/71 |
| 4,949,944 | 8/1990 | Groff, Sr. | 269/71 X |
| 5,160,125 | 11/1992 | Jenkins | 269/71 X |
| 5,362,021 | 11/1994 | Phillips | 5/658 X |

OTHER PUBLICATIONS

PEL Vertical Jig Vertical Fabricating Jig and Lutz Adapter Kit—p. 338.
Beckerv Orthopedic Model F1000 Orthotic Work Station—p. IV–2.
PEL Duplication Instrument Berkeley Horizontal Duplication Instrument—p. 339.
Hosmer Tools And Fabrication Supplies Vertical Fabricating Instrument—p. T–4.
Hosmer Tools And Fabrication Supplies Component Parts—p. T–5.
O & P Express Tools Vertical Fabricating Instrument—p. 579.
Blatchford Endolite Casting and Preparation.
M.E. Sampson & Associates Caliber™ Transfer Fixture.
Daw Ad Casting Stand And Arm Support.
Schein orthopadie service—p. 201.
Hosmer Tools And Fabrication Supplies Fabrication Fixtures—p. T–1.
Hosmer Tools And Fabrication Supplies Brim Adaptor and Adjustable Brims—p. T–2.
PEL Casting Tools—Perimeter Gauge Narrow Medial–Lateral Casting Brim p p. 312.
Hosmer Tools And Fabrication Supplies B & B Universal Casting Fixture—p. T–3.
Exhibit A.

*Primary Examiner*—Michael F. Trettel
*Attorney, Agent, or Firm*—Law Offices of Victor E. Libert; Frederick A. Spaeth

[57] ABSTRACT

A fabrication assembly (10, 18, 24, 30, 38, 44, etc.) for the manufacture of prosthetic and orthotic devices allows various components of these devices to be aligned on a common mast with respect to height, distance, flexion/extension, abduction/adduction and rotation alignment criteria, and each of these criteria can be adjusted apart from the other criteria. There are planar translation components (62, 62') that permit true planar, medial-lateral movement relative to a mast (10) without imposing rotation or angular deflection to a component mounted thereon. Accordingly, the assembly of a prosthetic or orthotic device according to physiological alignment criteria is an efficient step-by-step process, whereas prior art devices required that at least two criteria be adjusted and checked simultaneously. Among the features of the fabricating system are an angular/rotational fixture (38) that allows for separate settings of angular and rotational orientations for a given component. Also included is a casting apparatus (70) that has arm rests (100*a*, 100*b*) on which the patient can lean during the casting procedure, and which features separate height adjustments for each arm rest.

4 Claims, 8 Drawing Sheets

FABRICATING ASSEMBLY AND CASTING APPARATUS FOR PROSTHETIC AND ORTHOTIC DEVICES

BACKGROUND OF THE INVENTION

1. Field of the Invention

This invention relates to the manufacture of prosthetic and orthotic devices and, in particular, to a fabrication assembly useful for aligning the components of such devices during fabrication, and to a casting apparatus for making molds from which prosthetic components can be made.

Prosthetic and orthotic devices often comprise articulated components that must be properly aligned so that their movement conforms to the shape and movement mechanics of the wearer's body. For example, a prosthetic knee joint provides a pivoting motion between upper leg and lower leg components and the plane defined by the pivoting movement may have to be fixed at a particular angle with respect to the wearer's sagittal plane to maximize the comfort and ease of use of the prosthetic device. Similarly, in a prosthetic device for an above-knee amputee, the foot may have to be disposed at a suitable angle relative to the direction of travel and the leg prosthesis may have to conform to a wearer's flexion contracture, if any, and any indicated adduction or abduction contracture angles. To facilitate assembly of the device that conforms to the wearer's needs, the components of the device must be held in proper alignment while they are interconnected. The alignment criteria, e.g., height, angle, rotation, lateral displacement, etc., are derived from the wearer using anatomical references. For example, the alignment criteria for leg prostheses are typically reported with reference to the wearer's TKA (Trochanter-Knee-Ankle) reference line and/or the Ischium-Knee Center-Heel line in their respective planes. Conventionally, a technician employs a fabrication assembly comprising a vertical or horizontal mast and a plurality of clamps mounted on the mast for holding the various components of the prosthetic or orthotic device during the assembly process. There is a variety of commercially available fabrication assemblies of this kind.

2. Related Art

One prior art fabrication apparatus is sold under the tradename Hosmer Vertical Fabricating Jig VFJ-100. The Hosmer apparatus comprises a rod-like, vertically oriented mast on which a plurality of clamps is secured. The clamps can be moved vertically on the mast and serve to slidably receive horizontally disposed support arms that hold various tooling modules useful for engaging components of prosthetic or orthotic devices. The mast of the Hosmer apparatus is vertically slotted so that clamps can easily be aligned to dispose the horizontal support arms in a common, vertically oriented plane. Each support arm extends from a clamp to a fixed distance from the mast and has a rotational orientation within the clamp. To vary either the distance from a tooling module on a support arm to the mast or the rotational orientation of the module, it is necessary to loosen the clamp. In so doing, both the rotational orientation and distance attributes are released. Therefore, both attributes must be carefully measured after each time the clamp is re-tightened. Further, the mast, clamp and support arms of the Hosmer apparatus only permit the adjustment of two alignment criteria for prosthetic device components secured thereto: linear distance from the mast and rotational orientation relative to the mast. Accordingly, if it is necessary that one tooling module be laterally displaced relative to another, all that can be done using the Hosmer apparatus is to rotate the support arm holding the tooling module to be moved. However, this motion imposes a rotation on the tooling module that may be unwanted. Stated differently, if the mast is viewed as corresponding to the vertical axis of the patient's body (i.e., as corresponding to the intersection of the frontal and sagittal planes) and if the support arms are viewed as extending forward from the patient's body, the Hosmer apparatus does not provide for true medial-lateral movement. One support arm on the Hosmer apparatus is slotted so that it can be moved horizontally without losing its rotational orientation in the clamp, but it carries a tooling module attached thereto by a ball joint. Clearly, after loosening the ball joint to reposition a component secured in the tooling module, all rotational and angular orientations of the component in the tooling module must be checked before re-tightening the ball joint.

SUMMARY OF THE INVENTION

The present invention provides a fabrication assembly for facilitating the construction of prosthetic and orthotic devices. The assembly comprises a mast having a longitudinal mast axis and a plurality of tooling modules for engaging device components. There are coupling means for releasably securing the tooling modules to the mast at selectable alignment criteria corresponding to criteria selected from the group consisting of height, distance, angle and rotation relative to the mast axis. The coupling means of the present invention permits the user to set and release any one alignment criterion without releasing another.

According to one aspect of the invention, the assembly may comprise planar translation means for allowing the user to move a tooling module in a plane disposed in non-parallel relation to the mast axis while preserving the angular and rotational orientation of the component in the tooling module relative to the mast axis. For example, the planar translation means may allow the user to move a tooling module in a plane disposed in substantially perpendicular relation to the mast axis. In a particular embodiment, the planar translation means may comprise a first angled extensor and a second angled extensor. The first angled extensor may have a first end and a second end and a first extensor axis and may be dimensioned and configured to be mounted on the mast at the first end and to extend from the mast in the direction of the first extensor axis. The first angled extensor may have at its second end a first extensor receiver for receiving the second angled extensor therein in slidable, non-rotating, angled relation to the first extensor axis. The second angled extensor may have a second extensor axis disposed at an angle, preferably a right angle, relative to the first extensor angle, and also may have a second extensor receiver at the second end thereof, for receiving a tooling module therein that extends therefrom at an angle, preferably a right angle, relative to the second extensor axis.

According to another aspect of the invention, the coupling means may comprise an angular/rotational fixture for imparting at least one of a desired angle and rotation to a device component relative to the mast. The angular/rotational fixture may comprise a mounting portion for mounting the fixture to the mast, a component-engaging portion and a pivot-rotation linkage between the mounting portion and the component-engaging portion for independently permitting and preventing rotation and pivoting motions between the mounting portion and the component-engaging portion.

According to another aspect of the invention, the coupling means may comprise at least one receiving member and an associated extensor having a longitudinal extensor axis. The receiving member and the extensor may be dimensioned and configured so that the receiving member accepts the extensor for sliding motion therein and so that the extensor is indexably received in the receiving member with regard to rotation about the longitudinal extensor axis. Accordingly, the sliding motion of the extensor in the receiving member does not affect the rotational orientation of the extensor in the receiving member.

The present invention also relates to a casting apparatus for supporting a patient while a cast of a body part is being made. The casting apparatus comprises a mast and an arm rest support fixture movably mounted on the mast. The support fixture comprises two forearm rest pads and separate adjustment means for each rest pad whereby the height of each pad can be adjusted independently from the height of the other pad. Preferably, the mast is the sole supporting element in the apparatus so that a casting technician can have substantially unobstructed access to the patient's physique while the patient is supported by the apparatus. The casting apparatus may optionally comprise a pelvic support means on which the patient can support at least part of his or her weight.

DETAILED DESCRIPTION OF THE INVENTION AND PREFERRED EMBODIMENTS THEREOF

The fabrication assembly of the present invention provides to technicians responsible for the assembly of prosthetic and orthotic devices important features not attainable with prior art fabrication assemblies. One of these features is the accommodation of true medial-lateral movement of tooling modules, so that alignment specifications that call for medial-lateral movement of a component of such a device can be attained without imposing unwanted rotational movement on the component. Another feature of the present invention is that each of the various alignment criteria, e.g., height, distance, angle and rotation, of a prosthetic or orthotic component relative to the mast can be adjusted and varied independently of the others. For example, once a particular flexion angle is established for a particular component, that angle can be fixed and other adjustments such as height, distance, and medial-lateral position can be adjusted without having to re-measure the flexion angle.

Figure 1:
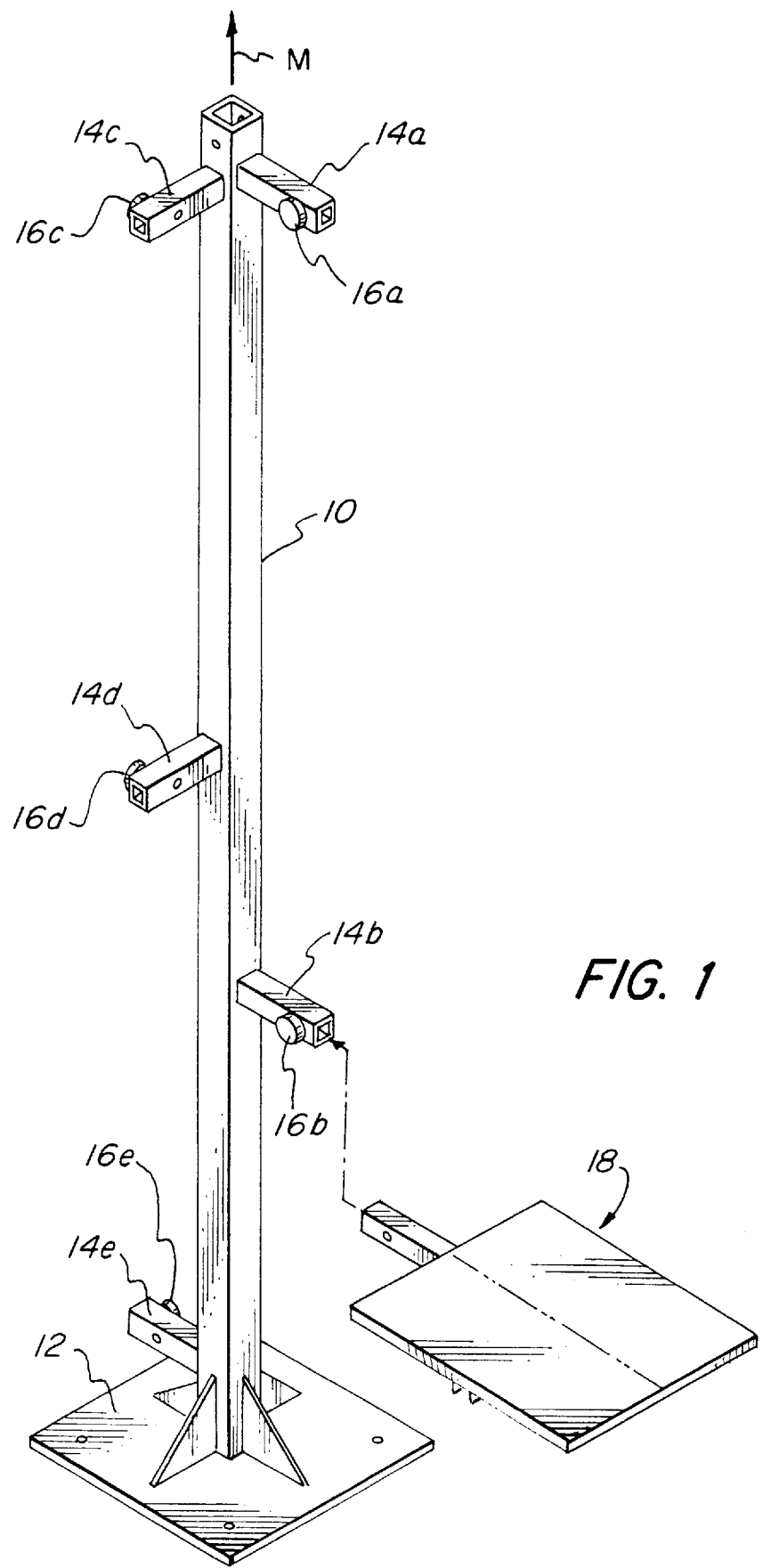
FIG. 1 is a perspective exploded view of a mast and a tooling module of a vertical fabricating system in accordance with a particular embodiment of the present invention, indicating one method for mounting the tooling module on the mast by inserting it into a receiver on the mast.

A fabrication assembly in accordance with one embodiment of the present invention comprises a mast member as shown in FIG. 1. Mast 10 is a straight, rigid member having a square external cross-sectional configuration. Mast 10 is secured to a base plate 12 at right angles thereto so that mast 10 can be fixedly disposed in a vertical orientation by securing base plate 12 to a horizontal stationary structure, such as a work bench or work place floor.

A fabrication assembly in accordance with the present invention further comprises coupling means for attaching tooling modules to the mast and for manipulating the modules into conformity with desired alignment criteria. Tooling modules are devices designed to engage components of prosthetic or orthotic devices. By manipulating a tooling module using the coupling means, a technician, i.e., the user of the fabrication assembly, can properly align the component engaged therewith. The coupling means may comprise a range of components that can be used singly or in various combinations, as discussed below.

The coupling means comprises receivers 14a, 14b, etc., which are fixedly attached to mast 10. Receivers 14a, 14b, etc., are tubular structures having square cross-sectional internal configurations and are therefore dimensioned and configured to slidably receive therein a square insert member to which a tooling module may be attached, as indicated for the tooling module comprising table attachment 18 (which is described more fully below), for linear sliding motion of the insert member in the receiver. The insert members are horizontally slidable within the receivers and therefore allow the technician to dispose a prosthetic component engaged thereon at a desired distance from the mast. Each receiver is equipped with a tightening knob mounted on a machine screw threaded through the receiver so that it can engage an insert member therein. When the tooling module is at the desired distance from mast 10, the knobs 16a, 16b, etc., can be turned until the machine screw bears on the insert member, to secure the insert member in the receiver. Generally, all receivers in the fabrication assembly of the present invention comprise a tightening knob or other securing means for securing an insert member therein. Since the insert member and the receiver are square in cross-sectional configuration, loosening a knob 16a, 16b, etc., to allow linear sliding motion of the insert member in the receiver does not affect the rotational orientation of the insert member in the receiver. If the insert member is withdrawn from the receiver, it may be rotated by 90° and re-inserted. Thus, the rotational orientation of the insert member is preserved but is indexably adjustable in the receiver.

Figure 3:
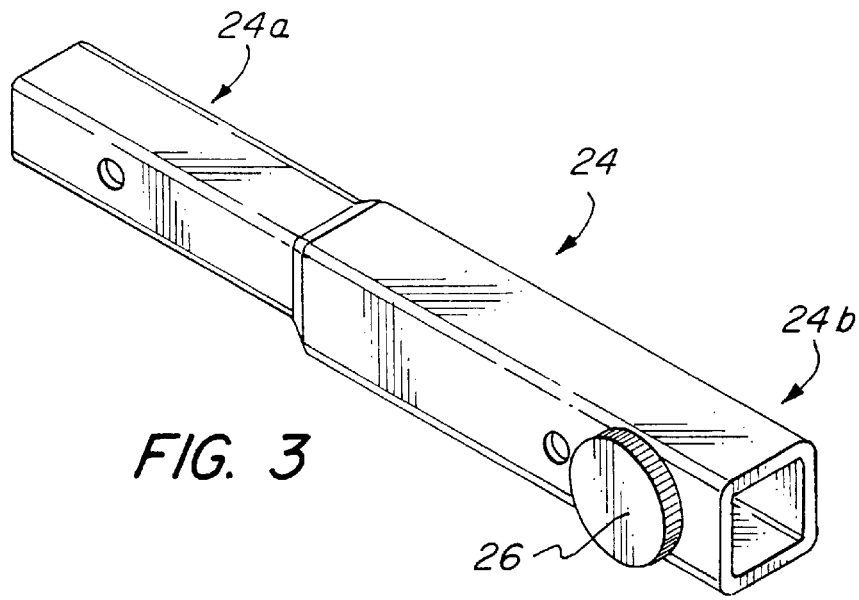
FIG. 3 is a perspective view of an extensor member for use in the present invention.
Figure 2:
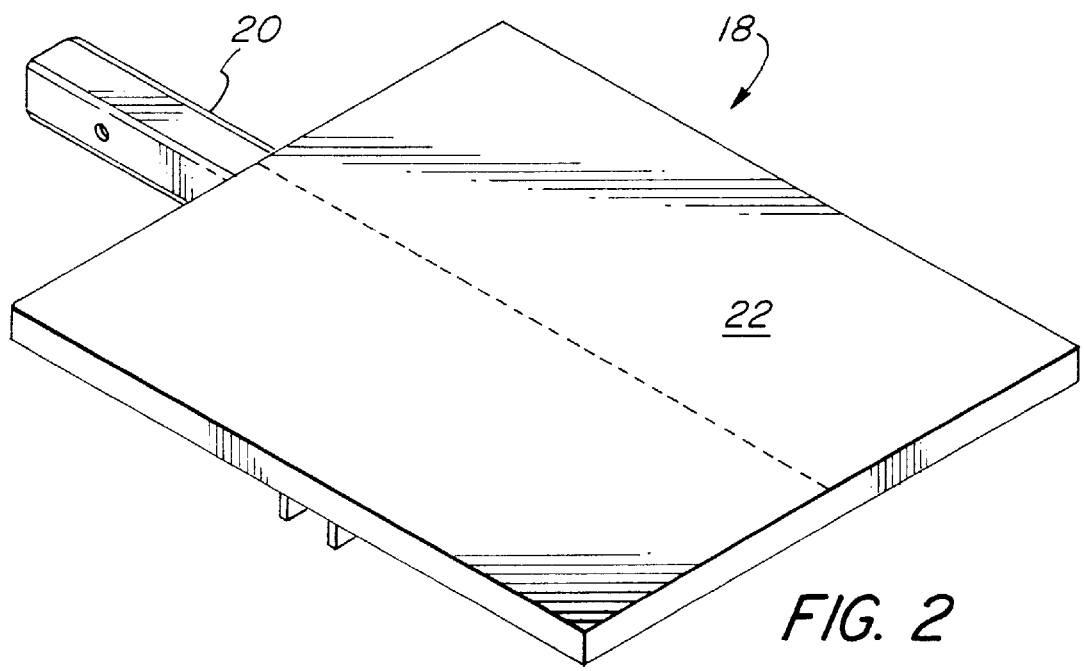
FIG. 2 is a perspective view of a table attachment for use in a fabricating system in accordance with the present invention.

The table attachment 18 of FIG. 2 is one species of tooling module which comprises an insert member 20 and a plate 22 secured thereto. When table attachment 18 is secured on mast 10 by inserting and securing the insert member 20 in a receiver, e.g., receiver 14b, plate 22 provides a stable, horizontal surface on which the technician may rest a component of a prosthetic device. Typically, table attachment 18 is used for the alignment of a prosthetic foot, with plate 22 simulating the floor on which the patient's prosthesis will rest. If insert member 20 and the associated receiver in which it is secured do not have adequate length to provide a distance from mast 10 that is appropriate or convenient for the assembly of a particular device, the technician may employ an extensor, such as extensor 24 shown in FIG. 3. Extensor 24 has a first end 24a that is dimensioned and configured to be slidably received within any one of receivers 14a, 14b, etc., and a second end 24b that is dimensioned and configured to receive insert member 20. Extensor 24 is equipped with a tightening knob 26 near second end 24b so that an insert member received therein can be securely retained. By the use of slidably received insert members and, when necessary, extensors, various tooling modules can be secured at desired distances from mast 10 and adjustments can be made to those distances without affecting the angular, rotational or height relationship of the tooling module to the mast.

Figure 4:
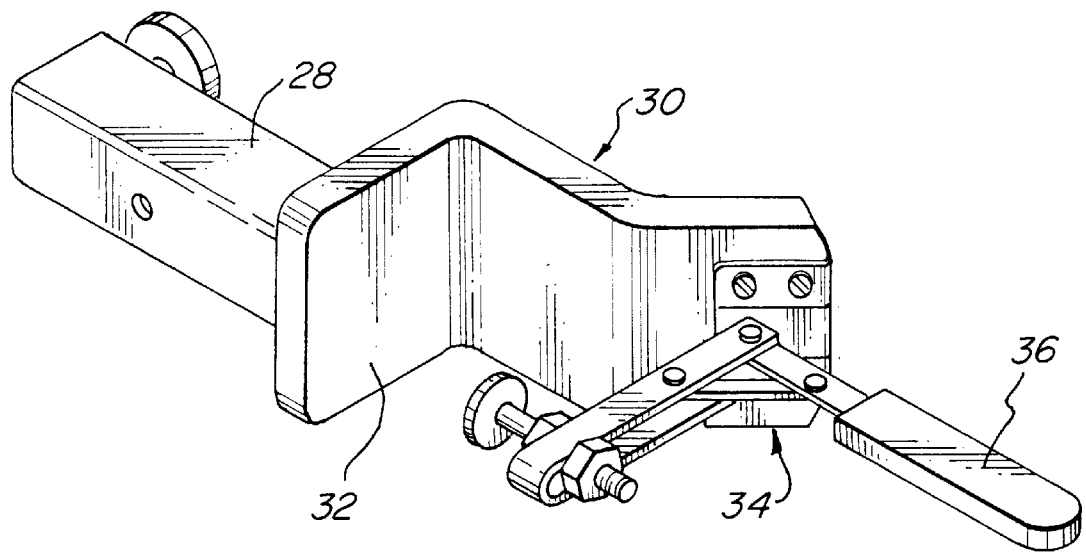
FIG. 4 is a perspective view of a movable receiver for a fabricating system in accordance with the present invention.

To allow height adjustments for tooling modules relative to the mast, the coupling means of the fabrication assembly of the present invention may comprise one or more movable receivers such as movable receiver 28 shown in FIG. 4. Receiver 28 has a rectangular internal configuration just as receivers 14a, 14b, etc. To render receiver 28 movable on mast 10, receiver 28 is equipped with a releasable engagement fixture 30. Engagement fixture 30 comprises an L-bracket 32 dimensioned and configured to engage two faces of rectangular mast 10 and a hand-operable clamp mechanism 34 by which a user can clamp L-bracket 32 against mast 10 to secure receiver 28 at a desired height on mast 10. Adjustment of the height of movable receiver 28 and any tooling module mounted thereon can be attained by manipulating lever 36 first to release the clamping force applied to mast 10 to allow movement of receiver 28 and then to re-apply the clamping force. By taking care to assure that L-bracket 32 fully engages the two sides of the mast regardless of its height on mast 10, the user can quickly and easily adjust the height of a tooling module without affecting other alignment criteria such as the medial-lateral placement or rotational orientation of the tooling module secured thereon.

It will now be clear that an extensor such as extensor 24 can be mounted in a movable receiver such as receiver 28 and that together, both the height of a tooling module mounted thereon and the distance of the tooling module from the mast can be independently adjusted, and that in adjusting one such alignment criterion, the other can be reliably maintained.

In addition to height and distance, the present invention allows for conformity with alignment criteria that require the imposition of an angular or rotational orientation to a prosthetic device component relative to the mast. Accordingly, the coupling means of the fabrication assembly in accordance with the present invention may comprise an angular/rotational alignment fixture such as fixture 38 shown in FIG. 5A. Angular/rotational fixture 38 comprises an insert member 20, a rotation member 40 and a pivot member 42. Attached to pivot member 42 is a tooling module 44 which comprises vise blocks 46a, 46b which are dimensioned and configured to receive a prosthetic or orthotic component such as a pipe or bar therebetween. Other tooling modules can be attached to the angular/rotational alignment fixture, e.g., the pipe clamp of FIG. 9A or any other tooling module, as desired. Rotation member 40 is mounted on a pintle (not shown) that allows rotation member 40 to rotate about the longitudinal axis L of insert member 20 as suggested by rotation arrow 48. Rotation member 40 carries a threaded pin 50 that extends therefrom in parallel relation to axis L of insert member 20. A threaded pin 50 passes through a curved slot in a flange 52 carried on insert member 20, the slot accommodating a typical range of rotational motion of rotation member 40. A tightening knob 54 is attached to threaded pin 50 and can be rotated so that knob 54 can be tightened to grip flange 52 when rotation member 40 is in a desired rotational configuration. In this way, the desired rotational configuration can be secured. Preferably, flange 52 and rotation member 40 bear graduations and a reference indicator so that a prescribed degree of rotation can easily be attained. Linearly moving parts such as insert members can likewise be marked with graduations so that their positions in receivers can similarly be quickly and easily attained or replicated.

Part of rotation member 40 forms a clevis comprising arms 56a, 56b through which a pivot bolt passes. Arms 56a and 56b receive between them pivot member 42, through which a pivot bolt (unnumbered) passes. Pivot member 42 is therefore able to pivot about the pivot bolt in a direction orthogonal to the rotation of rotation member 40, the pivot directions being upward and downward given the rotational orientation in the drawing. A tightening knob 60 is mounted on the pivot bolt and can be used to tighten arms 56a and 56b to secure pivot member 42 at a desired pivotal angle. Since knob 54 is used to release or secure the rotational orientation of fixture 38 and an independently operative knob 60 is used to secure the angular configuration of fixture 38, it will be clear that either one of the angular or rotational attributes of fixture 38 can be set, released and changed without affecting the other. This feature provides a significant improvement over the use of a ball joint to hold a tooling module. While a ball joint allows the technician to set both angular and rotational orientation for a tooling module, it cannot allow the user to set or change these criteria separately from each other. Once a ball joint is loosened, the ball therein is free to engage in both pivotal and rotational movement and before the joint is re-secured, both the angular and rotational orientations of the tooling module in the joint must be re-checked.

Figure 5A:
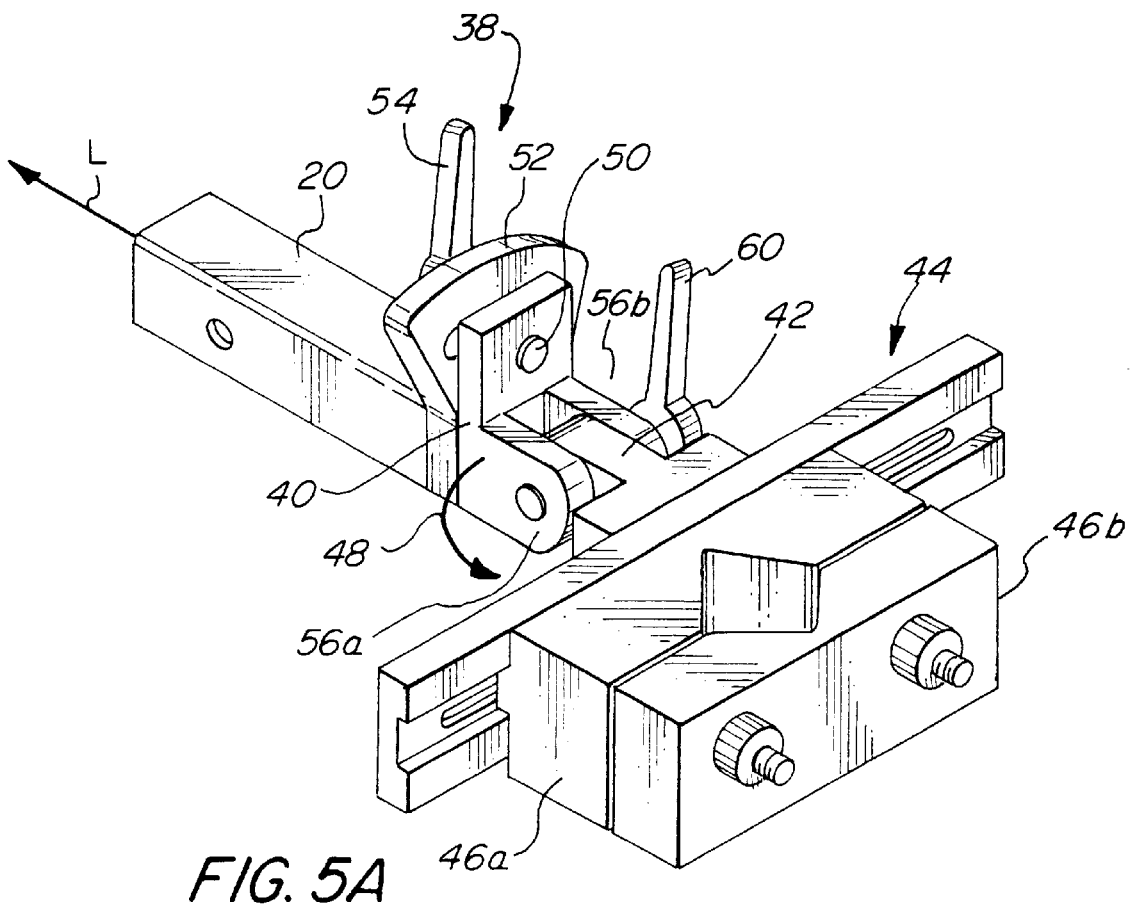
FIG. 5A is a perspective view of a tooling module mounted on an alignment/rotation fixture in accordance with the present invention.
Figure 5B:
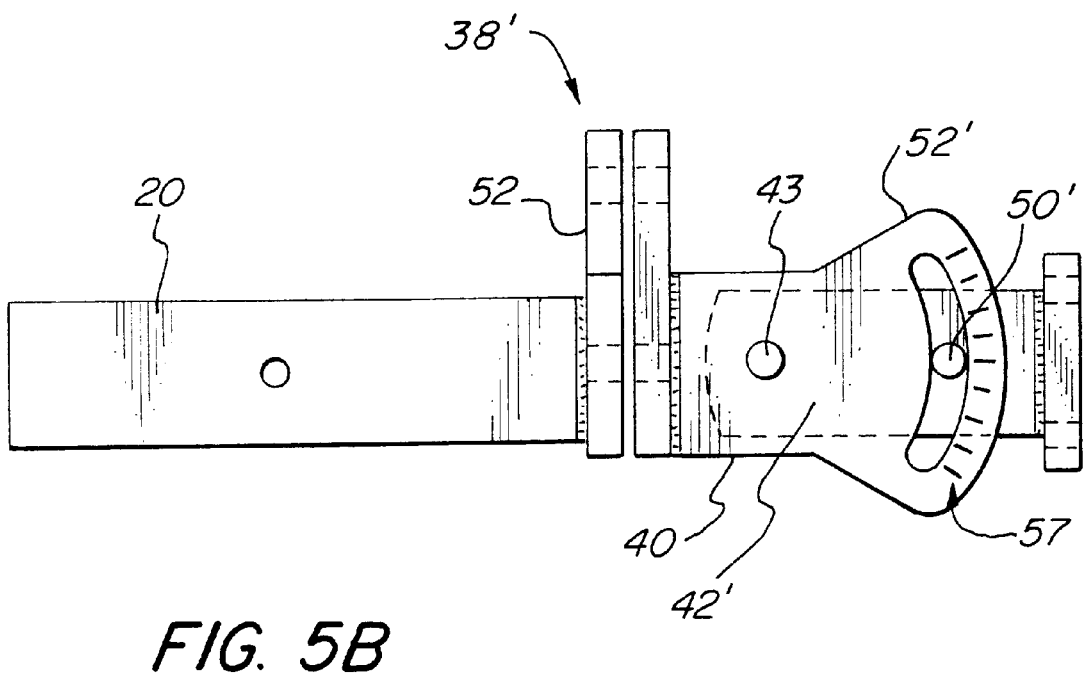
FIG. 5B is a schematic elevation view of an alterative embodiment of an angular/rotational alignment fixture in accordance with the present invention.

In a preferred embodiment, an angular/rotational fixture may be configured as shown in FIG. 5B. Angular/rotational fixture 38' comprises an insert member 20 and is configured similarly to angular/rotational fixture 38 except that the rotation member 40 comprises a slotted flange 52' similar to flange 52. Pivot member 42' pivots about pivot bolt 43 and comprises a threaded pin 50' that passes through the slot of flange 52'. A tightening knob (not shown) on pin 50' permits the user to fix the angle of pivot member 42' by bearing on flange 52', and flange 52' bears graduations 57, just as does flange 52 so that the angle of pivot member 42' can be recorded and easily replicated.

Figure 6:
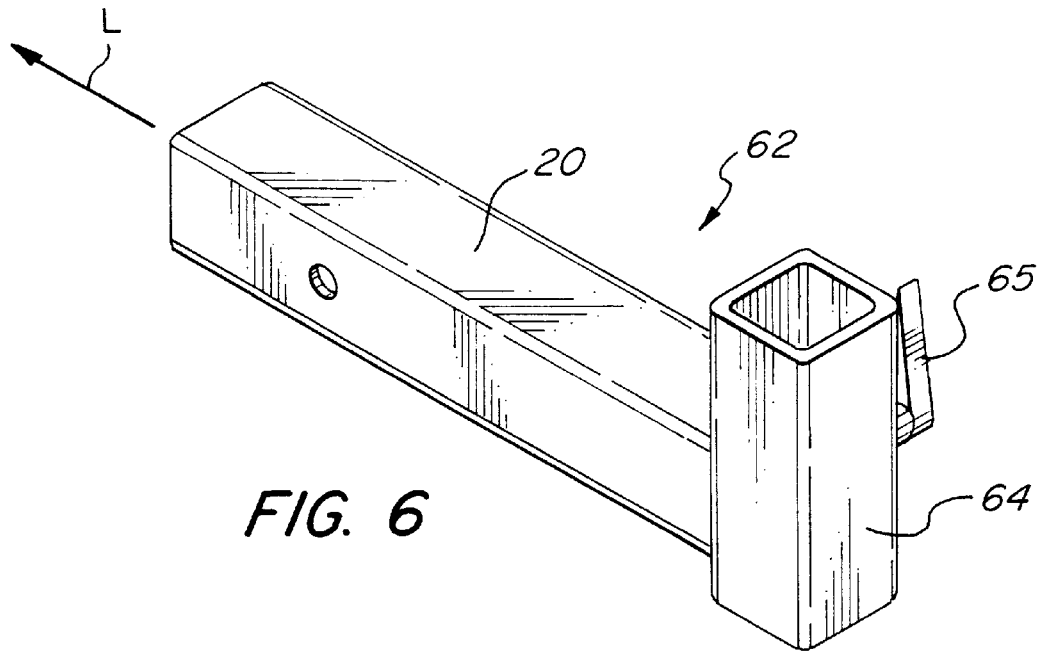
FIG. 6 is a perspective view of an angled extensor in accordance with the present invention.
Figure 7:
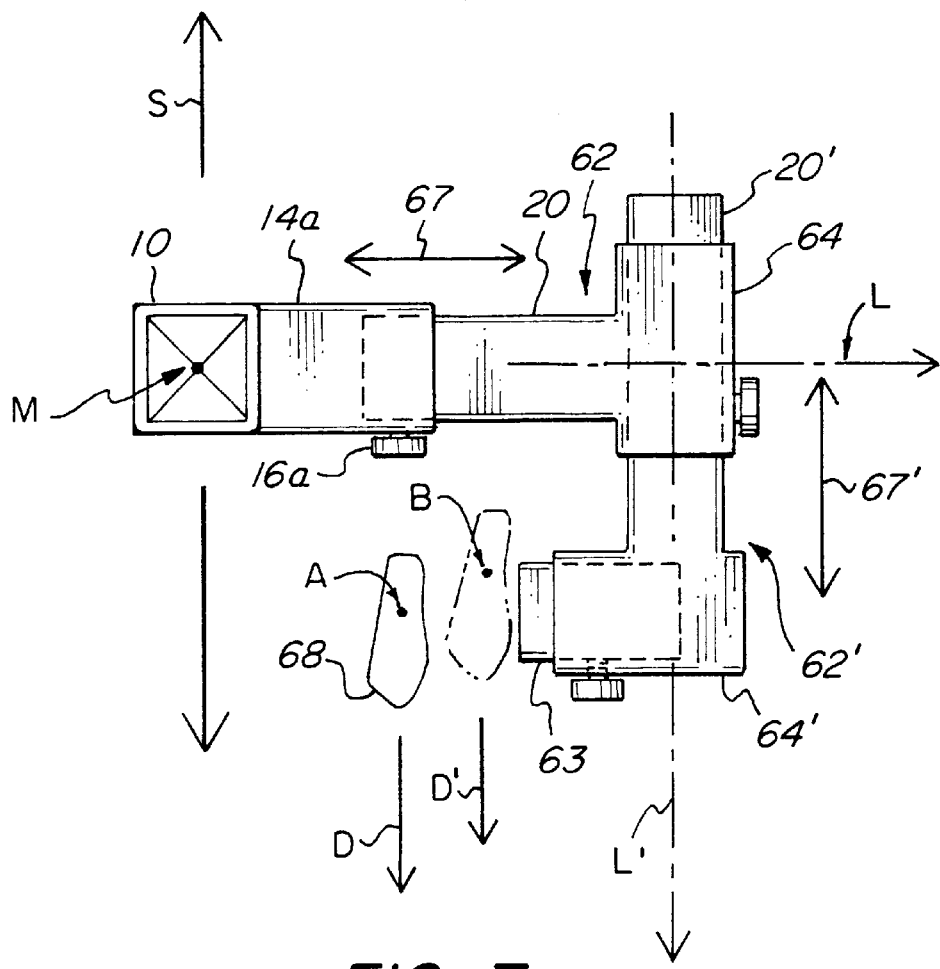
FIG. 7 is a schematic plan view of two angled extensors mounted on a mast in accordance with the present invention.

Preferably, the coupling means also comprises an angled extensor as shown in FIG. 6. Angled extensor 62 comprises an insert member 20 having a longitudinal axis L and, at one end thereof, an extensor receiver 64 which is dimensioned and configured to receive therein an insert member disposed at an angle with respect to longitudinal axis L. Preferably, extensor receiver 64 is configured to dispose an insert member therein at right angles to longitudinal axis L. Extensor receiver 64 is equipped with a tightening knob 65 to secure the insert member received therein. Angled extensor 62 can be used alone when necessary to mount a tooling module at right angles to a horizontal receiver. Such an arrangement would allow, for example, the angular/rotational fixture 38 of FIG. 6 to provide for a combination of flexion (provided by the movement of pivot member 42) and rotation about a vertical axis (provided by rotation member 40). However, angled extensor 62 is advantageously used in combination with a second angled extensor 62', both situated so that their receiving sleeves dispose an insert member therein in a common horizontal plane perpendicular to the vertical mast. For example, in an arrangement shown in the plan view of FIG. 7, in which mast 10 is shown in cross section, a combination of angled extensors 62 and 62' can be used to position a tooling module 63 indicated in dotted outline without any detail. Angled extensor 62 extends from mast 10 in the direction of its axis L and angled extensor 62' extends from angled extensor 62 in the direction of its axis L'. Axis L' is at an angle relative to axis L; specifically, a right angle. With tooling module 63 secured in extensor receiver sleeve 64', the position of a prosthetic component therein can be moved from one location to another in a plane perpendicular to the longitudinal axis M of mast 10, i.e., in the plane of the drawing, without disturbing the angular or rotational orientation of the component. Thus, component 68, which may be a prosthetic foot, can be moved laterally (by the motion of angled extensor 62 in receiver 14a indicated by arrow 67) and forward or rearward (by the motion of angled extensor 62' in extensor receiver 64 indicated by arrow 67') from position A to position B while its angular orientation measured as the direction of arrows D, D', which indicate the heel-ball axis of the foot relative to the direction of motion, i.e., to the sagittal plane (visible only as a line S in the plan view of FIG. 7), remains unchanged. Had the present invention made use of a cylindrical or tubular mast with clamps that can rotate about the mast (as with the Hosmer apparatus discussed above), not only would the rotation change the distance from the sagittal plane, it would also change the angular orientation of component 68 relative to the sagittal plane. With respect to a prosthetic foot, this would mean that in establishing a desired off-set from the sagittal plane, the technician using the prior art Hosmer apparatus would, in rotating a clamp about the mast, change the angle of the foot relative to the direction of motion. In contrast, this invention allows the technician to set the desired angle of the foot relative to the sagittal plane by adjusting tooling module 63 (which may comprise an angular/rotational fixture, discussed below) and then adjusting the distance of the foot from the sagittal and medial planes without having to reset the angle of the foot. Thus, the assembly of the present invention allows for true, independent medial-lateral (and/or posterior-anterior) movement, making the alignment procedure very straightforward and more efficient and accurate than the prior art Hosmer apparatus could allow. This improvement is especially important in cases where the wearer's needs dictate extreme alignment criteria. Further, the various insert members and receivers of the coupling means components are uniformly sized to allow interchangeability, so the technician has the option of using particular components such as the planar translation means for some tooling modules on the fixture but not for others, as desired. Thus, a knee joint tooling fixture for an above-knee prosthesis could be held by planar translation means while a table attachment could be inserted directly into a receiver on the mast for the foot.

In the specific embodiment described above, the mast and coupling means, i.e., receivers, insert members, angled extensors and angular/rotational fixtures, etc., have square cross-sectional configurations. Accordingly, these elements can be slid within or along each other without sacrificing other alignment criteria such as rotational or angular configuration. It is not necessary, however, that these various elements have square cross-sectional configurations; any configuration effective for slidably interrelating the various elements without permitting changes in angular or rotational configuration could be used in the practice of the present invention. For example, the mast, receivers, insert members, etc., could be tubular in configuration and could comprise longitudinal slots to be engaged by the coupling means to allow sliding motion without freeing the tubes for rotation. By providing angled extensors having such receivers and insert members, the applicant's assembly provides an advantage not found in the prior art, i.e., the ability to impose medial-lateral movement and similarly, anterior-posterior movement, without imposing unwanted rotation on a tooling module. Other configurations for receivers and insert members for use in angled extensors in accordance with the present invention include various polygonal cross-sectional configurations, e.g., rectangular, hexagonal, etc.

Figure 8:
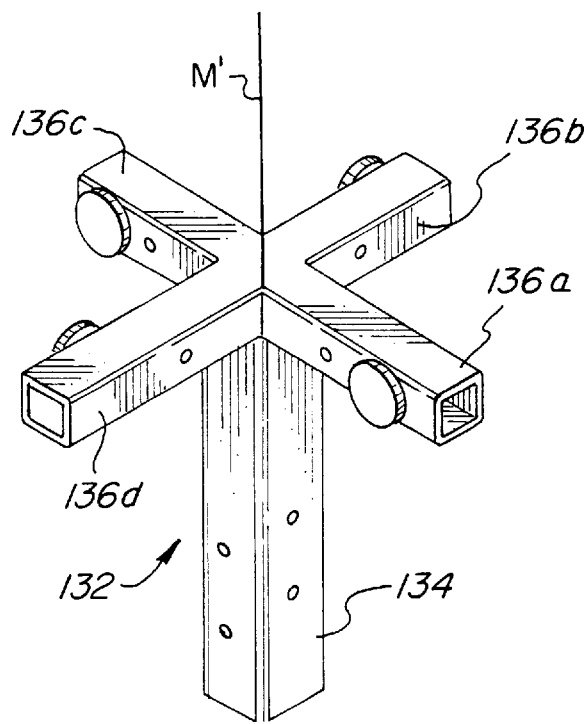
FIG. 8 is a perspective view of a head fixture for use in a fabricating system according to the present invention.

Other coupling means and tooling modules than those illustrated in FIGS. 1 through 7 may be used in accordance with the present invention. For example, FIG. 8 shows a multi-direction receiver head 132 that can be mounted atop a mast. The receiver head 132 has a trunk portion 134 having an axis M'. Trunk portion 134 engages mast 10 (FIG. 1) with axis M' in coaxial relation with mast axis M. Receiver head 132 has a plurality of receivers 136a, 136b, etc., disposed at various angles in a plane perpendicular to axis M'. Each receiver 136a, 136b, etc., is equipped with a tightening knob (unnumbered) to secure an insert member therein in the same manner as receivers 14a, 14b, etc., and knobs 16a, 16b, etc.

Figure 9A:
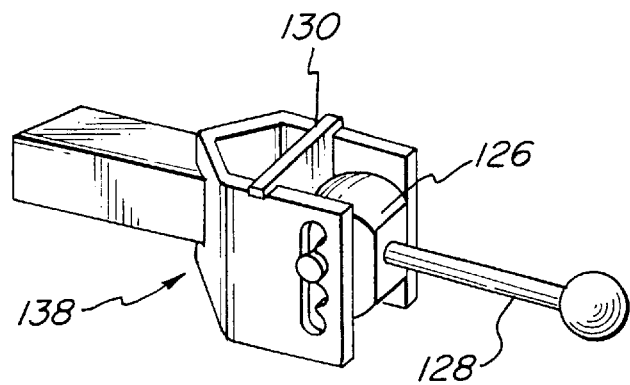
FIG. 9A is a perspective view of a pipe clamp for use in a fabricating system in accordance with the present invention.

FIG. 9A shows one variety of pipe clamp 138 that comprises a pivotable eccentric cam 126, for engaging prosthetic or orthotic components that have tubular members or "pipes". Cam 126 is equipped with a handle 128 and is dimensioned and configured so that in one orientation a pipe may be received between cam 126 and a fixed surface in the clasp such as pressure plate 130. Then, the technician may manipulate handle 128 to rotate cam 126 into a position in which it bears upon the pipe, thus securing the pipe between the cam and the pressure plate.

Figure 9B:
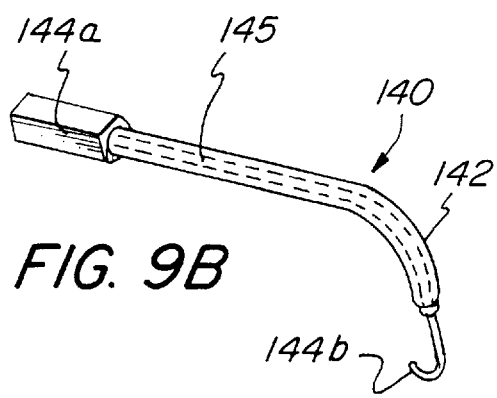
FIG. 9B is a perspective view of a spring hook for use in a fabricating system in accordance with the present invention.

FIG. 9B illustrates a spring cord attachment 140 comprising a curved tube member 142 having an insert member 144a at one end. A spring cord 145, shown in dotted outline, is secured within tube member 142 and terminates at the other end of tube member 142 in a hook 144b that is attached to the spring cord and which protrudes from the end of tube member 142. The technician can attach a prosthetic or orthotic component to hook 144b to suspend the component, when desired.

Figure 10:
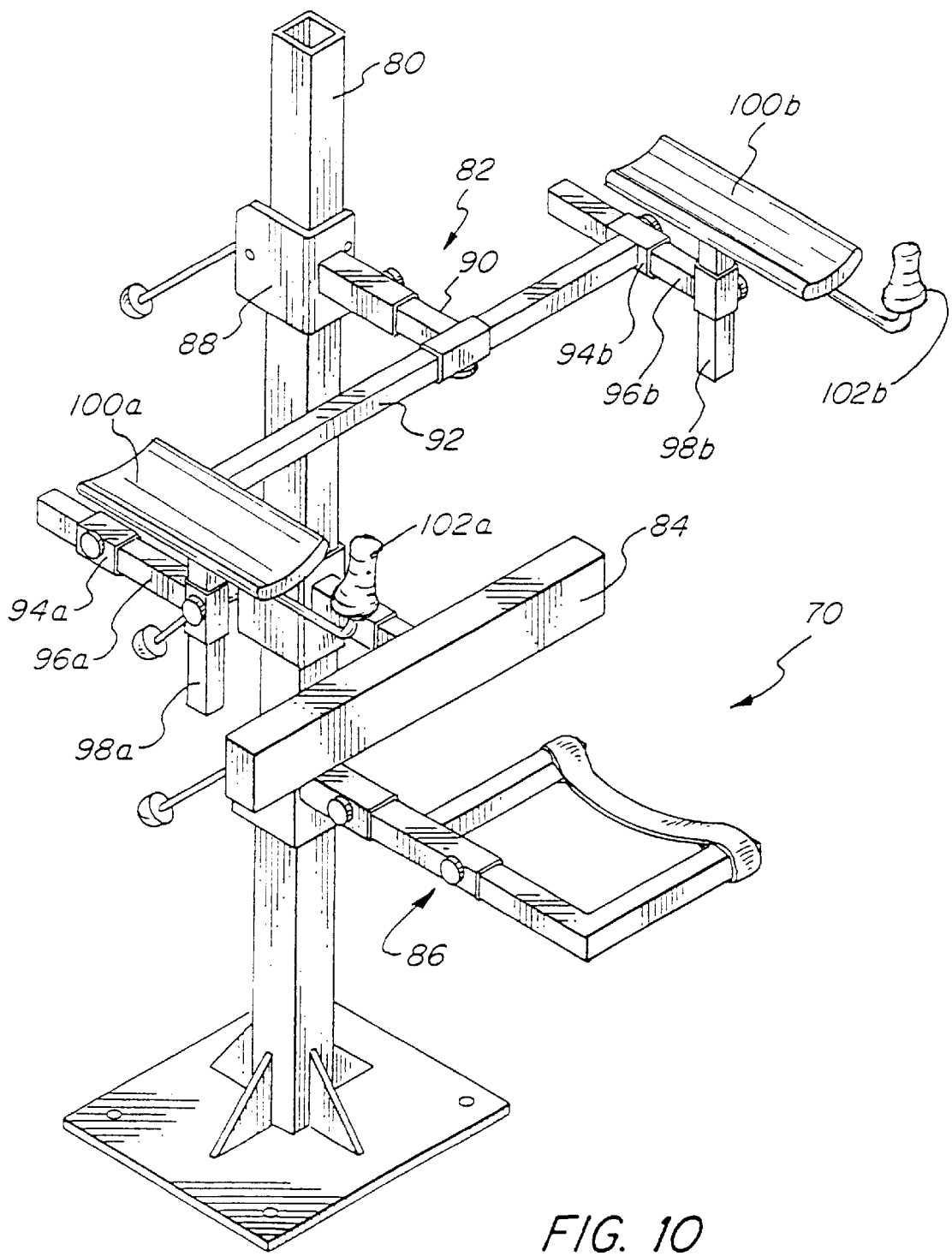
FIG. 10 is a perspective view of a particular embodiment of a casting apparatus in accordance with the present invention.

Part of the present invention also provides a casting apparatus as shown in FIG. 10. This casting apparatus 70 includes a mast 80, an arm rest support fixture 82, an optional pelvic rest 84 and a brim holder 86. Arm rest support fixture 82 is mounted on mast 80 by an adjustable receiver 88 which receives arm rest insert member 90. Arm rest insert member 90 carries a transverse bar 92 having two ends. At each end there is an angled receiver 94a, 94b which receives an angled extensor 96a, 96b, respectively. Each of the angled extensors 96a, 96b comprises a vertically oriented receiver for receiving forearm insert members 98a, 98b, respectively. On top of each forearm insert member 98a, 98b is mounted a forearm rest pad 100a, 100b on which the patient can rest his forearms during the casting procedure. Hand grips 102a, 102b are mounted on forearm rest pads 100a, 100b so that the patient can comfortably grasp the hand grips while his or her forearms are resting on the forearm pads 100a, 100b. Preferably, a patient sits or leans on pelvic rest 84 so that his or her posture does not degrade during the casting procedure. With the patient now properly and comfortably positioned, a cast can be made of a residual lower limb by securing a suitable quad brim in the brim holder. By using the separate forearm adjustments, the patient can be made more comfortable and the cast can be made more reliably because the patient can remain stationary for longer periods of time. Further, the illustrated casting apparatus is supported solely by a single support structure, i.e., by mast 80; there is no need for a cage-like structure to support the patient's body. Accordingly, it is very simple for a patient to manipulate himself, or for aids to help the patient manipulate himself on the device, and it is also easier for the casting technician to make a cast of the residual limb, since there are no interfering surrounding structures of the casting apparatus to obstruct access to the casting brim.

Figure 11:
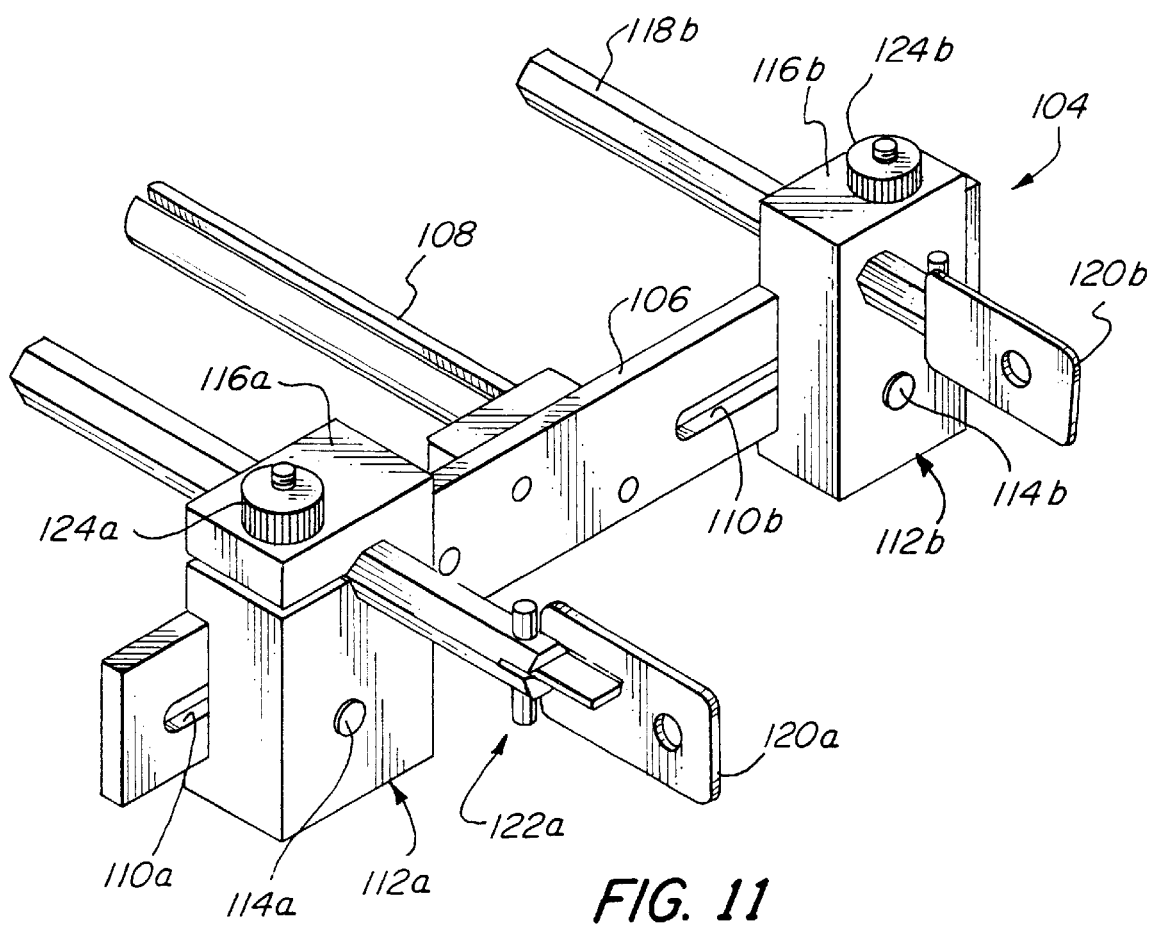
FIG. 11 is a perspective view of a joint tooling module in accordance with another aspect of the present invention.

A tooling module especially well-suited for engaging a joint of a prosthetic device is shown in FIG. 11. Joint tooling module 104 comprises a main slide bar 106 that is attached to a longitudinally grooved insertion rod 108 which extends perpendicularly from the approximate midpoint of main slide bar 106. At each end of main slide bar 106 there is a horizontal, longitudinally disposed slot 110a and 110b. The structures at each end of main slide bar 106 are substantially identical to one another, so only one of them will be described in detail with reference to indicator numerals that end in the suffix "a". Structures at the other end of main slide bar 106 that correspond to those described at the first end will bear like indicator numerals ending with the suffix "b". At the end of main slide bar 106 is a rod coupler 112a. Rod coupler 112a is slidably mounted on main slide bar 106 and comprises a securing bolt 114a that passes through slot 110a. A tightening knob is mounted on the end of bolt 114a but is not visible in the illustration. Rod coupler 112a can slide from side to side to the extent permitted by slot 110a and can be fixed in position by tightening the securing knob (not shown). The positions of rod coupler 112a and 112b can be interchanged; since each holds an aligning rod, in an off-center position, interchanging the rod couplers allows for width adjustment beyond the limits of slots 110a, 110b.

Rod coupler 112a comprises a grasping flange 116a that defines the hexagonal passage through coupler 112a. The hexagonal aligning rod 118a is received in the passage defined by grasping flange 116a and extends therethrough in perpendicular relation to main slide bar 106. An aligning tab 120a is pivotably mounted on the end of hexagonal aligning rod 118a. The pivot joint 122a is designed to have tight tolerances for a precision fit so that aligning tab 120a can be precisely positioned. The aligning tabs can be interchanged with others so that tabs specifically designed for various joints can be held on the aligning rod. A bolt extends upward through grasping flange 116a, and a tightening nut 124a can be tightened to secure the position of hexagonal aligning rod 118a therein. When tightening nut 124a is loosened, hexagonal aligning rod 118a can slide forward and backward in the passage defined by grasping flange 116a, but will nevertheless retain its rotational orientation within the passage. Likewise, the aligning rod and the associated tab can be removed from the coupler for facile engagement with a joint and the rod can be replaced in the coupler without loss of alignment. Accordingly, a standard alignment procedure can be followed regardless of the type of joint being used. In use, tooling module 104 can be mounted on mast 10 (FIG. 1) of the casting apparatus by inserting insertion rod 108 into a suitably configured receiver on the mast or on a suitable alignment fixture, e.g., an alignment fixture as shown in FIGS. 5A or 5B, while the alignment criteria are met. The user is thus relieved of the task of holding the module while positioning the joint. A prosthetic joint can be securely mounted in aligning tabs 120a and 120b. The joint tooling module allows the user to accurately align the joint.

EXAMPLE

The technician is assigned to assemble an endoskeletal above-the-knee prosthesis for the right leg. The patient has a flexion contracture of 10 degrees. He is bow-legged and has an adduction angle of 5 degrees. The patient's remaining foot is externally rotated 15 degrees from the line of progression. When the patient is in his natural standing posture, the right elbow is slightly elevated relative to the left elbow.

First, a cast is made of the patient's residual limb by seating the patient in the casting apparatus shown in FIG. 10. The height of arm rests 100a and 100b are separately adjusted to maximize the patient's comfort. The frontal and sagittal planes are marked on the cast. From the cast, a positive model of the residual limb is made, and the frontal and sagittal plane lines are transferred to the model. A pipe is installed in the model so that the model can be secured onto the vertical fabricating system of the present invention using a pipe clamp and angular/rotational fixture as shown in FIG. 5. The angular/rotational fixture allows the technician to place the mold in a vertical position despite any inadvertent angular off-set of the pipe in the model. When the model is secured in the vertical position, various standard adjustments are made to the model and a quad brim test socket is prepared. The test socket and other prosthetic components are mounted on tooling modules on the vertical fabricating system in a manner that meets the alignment criteria for the patient as described above. A table attachment tooling module is secured to the mast near the base plate to simulate a floor surface on which the prosthetic limb will rest. A prosthetic foot is secured in a tooling module that allows for rotation in a plane perpendicular to the axis of the mast so that the 15-degree external rotation can be achieved. A lower leg component and the test socket are mounted to the mast with tooling modules and angular/rotational fixtures so that the flexion contracture and adduction angle can be simulated. For example, the test socket is first disposed at a flexion angle of 10 degrees relative to the mast. This flexion angle is fixed and then the adduction of 5 degrees is imposed. The present invention allows the adduction angle to be adjusted without affecting the previously set flexion angle. The test socket may then be positioned through medial-lateral movement using angled extensors so that measurements complying with the patient's TKA alignment can be directly translated to the foot and the test socket using the mast as a reference. The fabricating assembly of the present invention allows the medial-lateral adjustment to be made without affecting the flexion or adduction adjustments previously made. Accordingly, this portion of the assembly procedure can be done more easily and efficiently than with any prior art fabricating system. When all the components of the prosthetic device are in proper alignment and the device is assembled, it is fitted to the patient. Any modifications that are required are noted. Once the fitting is satisfactory, a permanent prosthesis is assembled by repeating the assembly procedure for the test prosthesis. The height, angle, rotation, and other alignment criteria are easily replicated for the permanent device because of the superior design of the fabricating system of this invention.

In addition to the features and advantages described above, the fabricating system of the present invention allows for the simultaneous arrangement of more than one alignment set-up on a given mast. This is achieved by providing receivers that extend from the mast in different directions. Thus, receivers 14c and 14d extend in a common direction that is perpendicular to the direction of receivers 14a and 14b. Since mast 10 is square in cross-sectional configuration, receivers can be conveniently mounted thereon to extend from mast 10 in four directions. In addition, the head fixture shown in FIG. 8 can be used to supplement any receivers mounted along the length of the mast. This configuration allows two technicians to work simultaneously on different projects or, preferably, allows a technician to construct parallel alignment set-ups in which alignment criteria affixed in one set-up for a test device can be quickly transferred to a corresponding position in another set-up for the assembly of a final product. Alternatively, in the case of an orthosis, one set-up can be used to hold a model and the orthosis can be held in another set-up in which alignment configurations from the first set-up are easily transferred to the second. Such an arrangement vastly improves the efficiency and accuracy of the fabrication process.

While the invention has been described in detail with reference to particular embodiments thereof, it will be apparent that upon a reading and understanding of the foregoing, numerous alterations to the described embodiments will occur to those skilled in the art and it is intended to include such alterations within the scope of the appended claims.

What is claimed is:

1. A fabrication assembly for facilitating the construction of prosthetic and orthotic devices, comprising:

a mast having a longitudinal mast axis;

a plurality of tooling modules for engaging device components;

coupling means for releasably securing the tooling modules to the mast comprising;

a first angled extensor having a first and a second end and a first extensor axis, and a second angled extensor having a first and second end and a second extensor axis, the first end of the first angled extensor being dimensioned and configured to be mounted on the mast and to extend from the mast in the direction of the first extensor axis and the second end of the first angled extensor having a first extensor receiver for receiving the second angled extensor at the first end thereof in slidable, non-rotating angled relation to the first extensor axis, the second angled extensor being dimensioned and configured to extend from the first angled extensor along the second angled extensor axis;

the second angled extensor having at its second end a second receiver for mounting a tooling module therein, the second receiver being dimensioned and configured so that the tooling module therein extends at an angle relative to the second extensor axis.

2. A fabrication assembly for facilitating the construction of prosthetic and orthotic devices, comprising:

a mast having a longitudinal mast axis;

a plurality of tooling modules for engaging device components;

coupling means for releasably securing the tooling modules to the mast, wherein the coupling means comprises at least one receiving member and an associated slide bar having a longitudinal slide bar axis;

wherein the receiving member and the slide bar are dimensioned and configured so that the receiving member accepts the slide bar for sliding motion therein and so that the slide bar is indexably received in the receiving member with regard to rotation about the longitudinal slide bar axis so that the sliding motion does not affect the rotational orientation of the slide bar in the receiving member.

3. A fabrication assembly for facilitating the construction of prosthetic and orthotic devices, comprising:

a mast having a longitudinal mast axis;

an angular/rotational fixture comprising an insert member for mounting the fixture to the mast, a rotation member rotatably mounted on the insert member, a first tightening knob to secure the rotation member in a desired rotational configuration relative to the insert member, a pivot member pivotably mounted on the rotation member and a second tightening knob for securing the pivot member at a desired angular configuration relative to the rotation member; and a tooling module mounted on the pivot member for engaging device components;

wherein the fixture allows the user to independently permit and prevent mutually orthogonal rotation and pivoting motions between the insert member and the tooling module, and further comprising a first slotted flange on the insert member and a first pin on the rotation member, the first pin extending through the slot in the first flange, wherein said first tightening knob is mounted on the first pin, and further comprising a pivot bolt that connects the pivot member to the rotation member and wherein said second tightening knob is mounted on the pivot bolt.

4. A fabrication assembly for facilitating the construction of prosthetic and orthotic devices, comprising:

a mast having a longitudinal mast axis;

an angular/rotational fixture comprising an insert member for mounting the fixture to the mast, a rotation member rotatable mounted on the insert member, a first tightening knob to secure the rotation member in a desired rotational configuration relative to the insert member, a pivot member pivotably mounted on the rotation member and a second tightening knob for securing the pivot member at a desired angular configuration relative to the rotation member; and a tooling module mounted on the pivot member for engaging device components;

wherein the fixture allows the user to independently permit and prevent mutually orthogonal rotation and pivoting motions between the insert member and the tooling module, and further comprising a first slotted flange on the insert member, a first pin on the rotation member, the first pin extending through the slot in the first flange, wherein said tightening knob is mounted on the first pin, and further comprising a second slotted flange on the rotation member and a second pin on the pivot member, the second pin extending through the slot in the second flange, wherein said second tightening knob is mounted on the second pin.

* * * * *